US012357317B2

(12) United States Patent
Toscano et al.

(10) Patent No.: US 12,357,317 B2
(45) Date of Patent: Jul. 15, 2025

(54) OPTICALLY CLEAVED CATHETER COILING SYSTEM

(71) Applicants: Daniel Toscano, Wantagh, NY (US); Timothy White, Long Island City, NY (US)

(72) Inventors: Daniel Toscano, Wantagh, NY (US); Timothy White, Long Island City, NY (US)

( * ) Notice: Subject to any disclaimer, the term of this patent is extended or adjusted under 35 U.S.C. 154(b) by 207 days.

(21) Appl. No.: 18/049,059

(22) Filed: Oct. 24, 2022

(65) Prior Publication Data
US 2024/0130733 A1   Apr. 25, 2024
US 2024/0225656 A9   Jul. 11, 2024

(51) Int. Cl.
*A61B 17/12* (2006.01)

(52) U.S. Cl.
CPC .... *A61B 17/12113* (2013.01); *A61B 17/1214* (2013.01); *A61B 2017/12072* (2013.01)

(58) Field of Classification Search
CPC .......... A61B 17/12113; A61B 17/1214; A61B 2017/12072; A61B 2017/12068; A61B 2017/12077; A61B 18/22–26; A61F 2002/9505
See application file for complete search history.

(56) References Cited

U.S. PATENT DOCUMENTS

| 4,886,490 | A | * | 12/1989 | Shiber | ........................ | F16C 1/02 604/22 |
| 5,108,407 | A | * | 4/1992 | Geremia | .......... | A61B 17/12022 606/1 |
| 5,443,454 | A | * | 8/1995 | Tanabe | ............. | A61B 17/12195 604/82 |
| 6,240,630 | B1 | | 6/2001 | Lee et al. | | |
| 10,003,168 | B1 | | 6/2018 | Villeneuve | | |
| 2007/0100235 | A1 | | 5/2007 | Kennedy | | |

(Continued)

FOREIGN PATENT DOCUMENTS

CN   2901642 Y   *   5/2007

OTHER PUBLICATIONS

Pulsed Fiber Lasers from ns to ms range and their applications (Year: 2010).*
Espacenet translation of CN2901642Y (Year: 2007).*

*Primary Examiner* — Katherine H Schwiker
*Assistant Examiner* — Zehra Jaffri
(74) *Attorney, Agent, or Firm* — Bruce A. Lev

(57) ABSTRACT

Provided herein are catheter assemblies with detachment means for delivering implants. A method for coil embolization using a catheter includes: inserting a catheter into a patient intravenously or intraarterially; navigating the catheter to an aneurysm, the catheter defining an outer wall; placing a tip of the catheter at an opening of the aneurysm; delivering into the aneurysm, via pusher wire, through a lumen of the catheter, a coil; determining a user defined detachment point at which a distal coil segment of the coil should be detached from the coil; aligning the user defined detachment point of the coil with a designated detachment zone at the tip of the catheter; and toggling a laser source connected to the embedded optical fiber, thereby detaching the distal coil segment from the coil via an embedded laser beam emitted from the optical fiber at the designated detachment zone at the tip of the catheter.

6 Claims, 5 Drawing Sheets

(56) References Cited

U.S. PATENT DOCUMENTS

2018/0338767 A1* 11/2018 Dasnurkar ....... A61B 17/12168
2019/0231362 A1 8/2019 Maitland et al.
2020/0405390 A1 12/2020 Dzerins et al.

* cited by examiner

OPTICALLY CLEAVED CATHETER COILING SYSTEM

FIELD OF THE INVENTION

This application relates generally to catheter assemblies and the detachment mechanisms used when delivering implants, such as microcatheters used in coil embolization and other catheter-based implant procedures.

BACKGROUND

A catheter is a tubular medical instrument used for a wide variety of applications. Varying applications of catheters share that the catheter is inserted into the body. Once inside the body, depending on the toolkit of the catheter, the catheter can be used for treatment, surgical procedures, or diagnoses. A subcategory of catheters are microcatheters, typically having a diameter of less than two millimeters, designed primarily for endovascular procedures. One such endovascular procedure that utilizes microcatheters in the treatment of aneurysms is coil embolization, which will be used as an exemplary procedure to describe embodiments of the invention disclosed herein.

Aneurysms are abnormal ballooning or widening of an artery wall that may result in internal bleeding or worse. The nature of aneurysms and endovascular systems causes treatments to be tedious and specialized to each patient, especially in the case of a brain aneurysm. Previously, invasive surgeries were used to treat brain aneurysms, but in recent decades, noninvasive treatments have been developed. Coil embolization is a procedure that addresses aneurysms by using a microcatheter to insert metal wire segments into the aneurysm to form a blood clot and obstruct abnormal blood flow. The metal wire segments are typically manufactured with designated detachment zones. Requiring these designated detachment zones cause issues described in further detail below.

There are other procedures that utilize catheter delivered implants as well. Due in large part to their non-invasiveness, catheter-based implant procedures are desirable alternative procedures when compared to traditional surgical treatments. The advancement of medicine looks to minimize invasive procedures, which will continue to popularize and necessitate the use of catheter-based implants.

SUMMARY

In general, embodiments of the present disclosure provided herein include a modified catheter assembly, wherein the catheter is modified to comprise at least an optical fiber connected to a laser source.

In an exemplary embodiment, the catheter is a microcatheter. The optical fiber is connected to a laser source that, when activated, is used as a detachment mechanism during a catheter-based implant procedure.

In some embodiments, the optical fiber is embedded into the outer wall of the catheter, the optical fiber is notched or cut at the distal end such that the laser from the laser source emits through the notch or cut for the purpose of selectively cutting an object or material being passed through distal the end of the catheter.

In an exemplary embodiment, the modified microcatheter disclosed herein is used in a coil embolizing procedure wherein the optical fiber connected to a laser source is used as a laser cutting detachment mechanism used to segment coils during the procedure.

In another embodiment, the present disclosure relates to a method of detachment for a catheter based implant procedure, wherein the catheter is modified to comprise at least an optical fiber, the optical fiber being notched or cut at the distal end, the optical fiber being connected to a laser source, wherein the laser is activated such that the laser is emitted through the notch or cut at the distal end of the optical fiber and used to cause detachment of the implant.

In another embodiment, the present disclosure relates to a method of manufacture of a catheter, wherein the catheter comprises at least an optical fiber with a notch or cut made at the distal end, wherein the optical fiber is configured to be connected to a laser source capable of cutting implants used in catheter-based implant procedures.

In one embodiment, the microcatheter is an industry standard microcatheter comprising at least an outer wall, a pusher wire interior to the outer wall, and an optical fiber. The optical fiber is embedded in the wall of the microcatheter. At the proximal end, the optical fiber is connected to a laser source. At the distal end, the optical fiber reaches to the tip of the microcatheter and has an exposed portion. The optical fiber is notched/cut at the exposed portion so that the laser passed through the optical fiber is emitted through the notch/cut and directed towards the interior or the tip of the microcatheter. The emitted laser is used to selectively cut objects or materials passing through the tip of the microcatheter, thus serving as a detachment mechanism.

The above summary is provided merely for purposes of summarizing some example embodiments to provide a basic understanding of some aspects of the present disclosure. Accordingly, it will be appreciated that the above-described embodiments are merely examples and should not be construed to narrow the scope or spirit of the present disclosure in any way. It will be appreciated that the scope of the present disclosure encompasses many potential embodiments in addition to those here summarized, some of which will be further described below. Other features, aspects, and advantages of the subject matter will become apparent from the description, the drawings, and the claims.

Embodiments provided herein include a catheter including: an outer wall; a pusher wire surrounded, at least in part, by the outer wall; and an optical fiber having a distal end embedded in the catheter, where an exposed portion of the distal end of the optical fiber defines at least one of a notch or an angled cut such that a laser beam passed through the optical fiber is emitted inwards from the distal end to cut an object or material being passed through a distal tip of the catheter. According to some embodiments, the catheter is a microcatheter configured for catheter delivered implants. According to certain embodiments, an outer diameter of the distal tip of the catheter is between 1.0 Fr and 4.0 Fr. According to some embodiments, a length of the microcatheter is between 50 cm and 200 cm. The catheter of some embodiments includes a steerable tip. Embodiments optionally include a laser source connected to the optical fiber, where the laser source is a ytterbium nanosecond pulse fiber laser.

Embodiments provided herein include a method of coil embolization using a catheter, the method including: inserting a catheter into a patient intravenously or intraarterially; navigating the catheter to the site of an aneurysm, the catheter defining an outer wall; placing a tip of the catheter at an opening of the aneurysm; delivering into the aneurysm, via pusher wire, through a lumen of the catheter, a coil; determining a user defined detachment point at which a distal coil segment of the coil should be detached from the coil; aligning the user defined detachment point of the coil with a designated detachment zone at the tip of the catheter where an exposed portion of an embedded optical fiber is located, where the optical fiber defines at least one of a notch or an angled cut in the exposed portion; and toggling a laser source connected to the embedded optical fiber, thereby detaching the distal coil segment from the coil via an embedded laser beam emitted from the optical fiber at the at least one of the notch or the angled cut to the designated detachment zone at the tip of the catheter.

According to some embodiments, the catheter is a microcatheter configured for catheter delivered implants. According to certain embodiments, an outer diameter of a distal end of the microcatheter is between 1.0 Fr and 4.0 Fr. According to some embodiments, a length of the microcatheter is between 50 cm and 200 cm. The catheter tip of an example embodiment includes a steerable tip. The laser source connected to the embedded optical fiber is, in some embodiments, a ytterbium nanosecond pulse fiber laser. The coil of an example embodiment is made of at least one of a platinum or other metal alloy potentially with embedded gel substance.

Embodiments of the present disclosure include a system including: a catheter defining a distal tip; and a laser source, where the catheter includes: an outer wall; a pusher wire interior to the outer wall; and an optical fiber embedded within the catheter, where an exposed portion of the distal end of the optical fiber defines at least one of a notch or an angled cut such that a laser beam passed through the optical fiber is emitted inwards from the at least one of the notch or the angled cut to cut an object or material being passed through the distal tip of the catheter, where the laser source is connected to the optical fiber embedded within the catheter.

According to certain embodiments, the catheter is a microcatheter configured for catheter delivered implants. An outer diameter of the distal tip of the microcatheter is, in some embodiments, between 1.0 Fr and 4.0 Fr. A length of the microcatheter of some embodiments is between 50 cm and 200 cm. The catheter of an example embodiment includes a steerable tip. The laser source connected to the optical fiber is, in some embodiments, a ytterbium nanosecond pulse fiber laser. The laser source of an example embodiment is configured to output a laser with a fixed pulse of about 100 nanoseconds with about 1 milli-Joule pulse energy.

DETAILED DESCRIPTION

Figure 1:
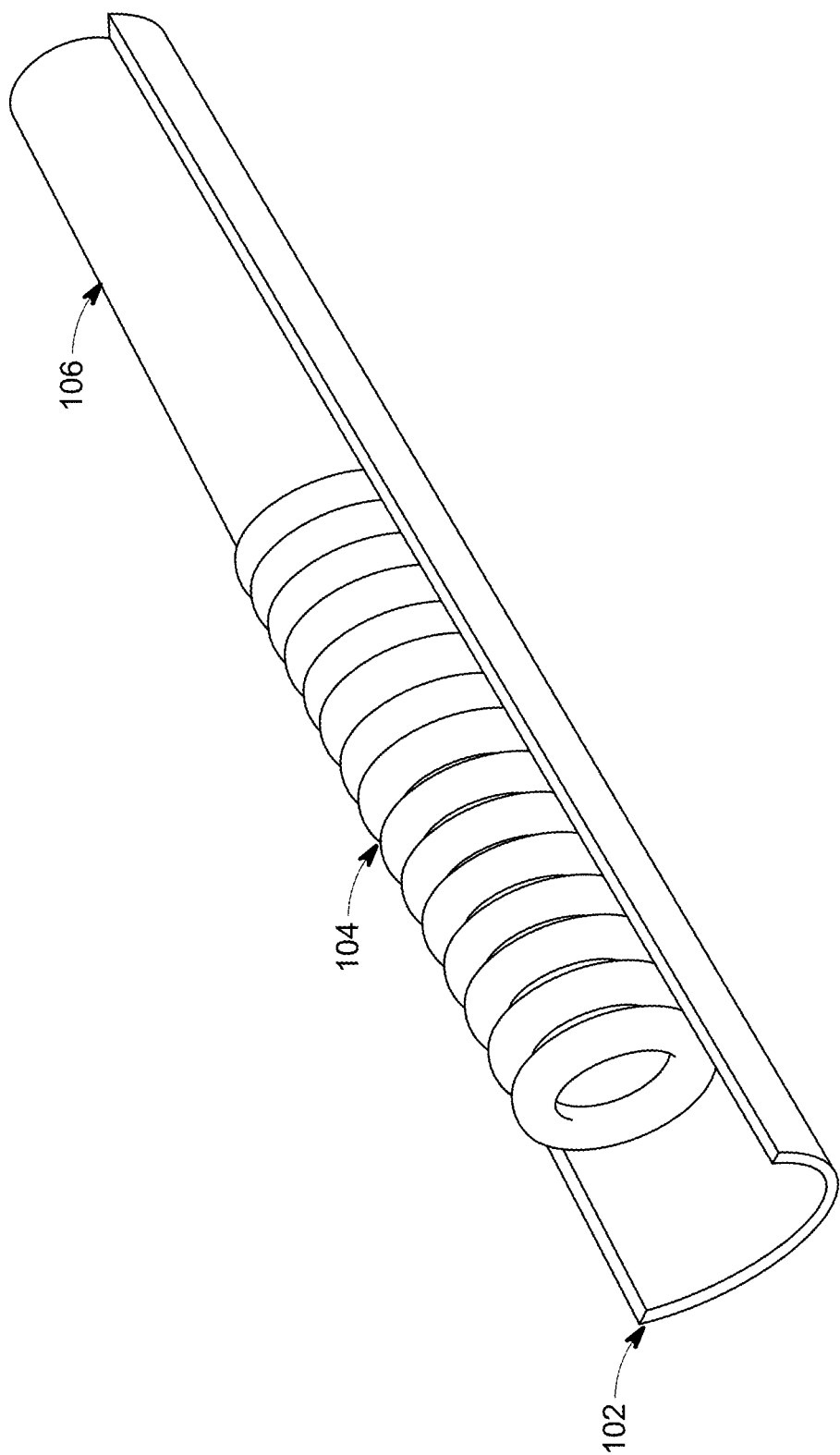
FIG. 1 is an example of a catheter standard in the industry with the top outer wall removed such that the internal structure may be seen.

Some example embodiments of the present disclosure will now be described more fully hereinafter with reference to the accompanying drawings, in which some, but not all, embodiments of the inventions are shown. Like reference numerals refer to like elements throughout. Indeed, various embodiments of the present disclosure may be embodied in many different forms and should not be construed as limited to the embodiments set forth herein.

As used herein, the terms "catheter" and "microcatheter" may be used interchangeably. Any embodiment described herein as either a "catheter" or "microcatheter" is not necessarily to be construed as exclusionary to the other. Various implementations familiar to one of ordinary skill in the art will appreciate that the methods and apparatuses disclosed in the present invention may be applicable to a variety of sizes and types of catheters.

As used herein, the terms "laser," "light," "beam," etc. may be used interchangeably to generically describe the portion of the electromagnetic spectrum where lasers operate (infrared, visible, ultraviolet) and their output.

As used herein, the word "example" or "exemplary" is used herein to mean "serving as an example, instance, or illustration." Any implementation described herein as "example" or "exemplary" is not necessarily to be construed as preferred or advantageous over other implementations.

As used herein, terms such as "front," "rear," "top," "proximal," "distal," etc. are used for explanatory purposes in the examples provided below to describe the relative position of certain components or portions of components. As used herein, the term "or" is used in both the alternative and conjunctive sense, unless otherwise indicated. The term "along," and similarly utilized terms, means near or on, but not necessarily requiring directly on an edge or other referenced location. The terms "approximately," "generally," and "substantially" refer to within manufacturing and/or engineering design tolerances for the corresponding materials and/or elements unless otherwise indicated. The use of such terms is inclusive of and is intended to allow independent claiming of the specific values listed. Thus, use of any such aforementioned terms, or similarly interchangeable terms, should not be taken to limit the spirit and scope of embodiments of the present disclosure.

The figures are not drawn to scale and are provided merely to illustrate some example embodiments of the inventions described herein. The figures do not limit the scope of the present disclosure or the appended claims. Several aspects of the example embodiments are described below with reference to example applications for illustration. It should be understood that numerous specific details, relationships, and methods are set forth to provide a full understanding of the example embodiments. One having ordinary skill in the relevant art, however, will readily recognize that the example embodiments can be practiced without one or more of the specific details or with other methods. In other instances, well-known structures and/or operations are not shown in detail to avoid obscuring the example embodiments.

In the present disclosure, apparatuses and methods are described to improve on existing catheter assemblies, particularly, microcatheters designed for endovascular procedures requiring catheter delivered implants.

Microcatheters are commonly used in a variety of medical procedures, having the ability to replace invasive surgical operations with noninvasive, interventional, or diagnostic procedures. Microcatheters are often used to navigate arteries/veins within the body for various procedures.

One exemplary procedure that requires a microcatheter delivered implant is coil embolization for the treatment of an aneurysm. Typically, a microcatheter is passed through the arteries of a patient and navigated to the site of the aneurysm. Thin metal coils are delivered through the microcatheter and inserted into the aneurysm in an effort to create a blood clot and cease abnormal blood flow into the aneurysm. Segments of the coil must be detached from the coil as they are inserted into the aneurysm.

Existing aneurysm coiling systems use a variety of detachment methods including but not limited to mechanical, electrolytic, fusible-link, etc. The presence of a single, fixed, detachment zones inherently sets the size of the delivered coil and introduces risk of improper coil size as well as deformation or premature detachment of the coil.

Often, aneurysms are occluded using multiple coils, progressing from framing to packing. As aneurysm packing progresses, coil deployment comes with increased risk of aneurysm rupture or coil herniation into the parent vessel. If the coil is partially deployed and the remaining coil length is deemed to large to continue placing, then an attempt to recapture the coil can be attempted, although may not be successful and comes with risk of dislodging the coil mass or losing the position of the microcatheter within the aneurysm therefore reintroducing the risk of re-accessing the aneurysm.

The ideal coiling setup for each aneurysm differs due to changes in location, vessel size, neck/dome size, orientation, and the like. There exists an essentially infinite number of possible anatomic variations. Manufacturing per-patient perfect length fixed detachment coils is not physically possible. Instead, many different shapes and lengths are manufactured and then often stuck in hospital inventory awaiting use.

In general, there is a need for a detachment mechanism for catheter-based implants that allows user defined detachment at any point. Specifically, these issues and others pose a need for a detachment mechanism for use in coil embolization that allows for user defined coil segment lengths and a coil that is free of fixed detachment zones.

Microcatheters are complex tools to manufacture, but their widespread useability has made them standard in the medical industry. A variety of applications and use cases motivate manufacturers to develop microcatheters with varying physical properties and toolkits. However, generally, microcatheters embody some standards that will be described in further detail below. It should be appreciated that this is for illustrative purposes and is not meant to be construed as a limitation of the present disclosure. Those of ordinary skill in the art will appreciate that catheters comprising variations or contradictions to the following generalizations are not limiting to the application of the modified catheter disclosed herein.

Microcatheters have a proximal end, a middle section, and a distal end with a tip. The full length of a microcatheter is approximately less than 200 cm, but more than 50 cm. Each zone has a smaller outer diameter than the zone proximal to it, such that the distal end and tip have the smallest outer diameter (approximately 1.6 Fr to 4.0 Fr), while the proximal end has the largest outer diameter (approximately 2.0 Fr to 6.0 Fr). The interior of the entire microcatheter has a constant diameter. The tip of the microcatheter may be fixed at an angle, or for improved navigation, an integrated steerable tip may be used where the user can control the shape of the tip in real time. The wall of the microcatheter may comprise several layers. An injection molding system may be used to create an outer most layer with a hydrophilic coating that helps the microcatheter maneuver intravenously or intraarterially. Layers interior to the outer most layer may provide kink-resistance and structural support for the microcatheter. Typically, different sections along the length of the microcatheter comprise varying layers to achieve varying physical properties. For example, in one such layer, braided wires are wrapped along the microcatheter in varying fashions, such as a single braiding, double braiding, parallelly, perpendicularly, etc., to achieve distal sections that are more flexible than those proximal. Interior to the wall, a pusher wire runs through the lumen of the microcatheter from the proximal end to the tip at the distal end. The length of the pusher wire exceeds the length of the microcatheter and allows the user to deliver implants and generally interact.

In the example of a coil embolizing procedure, the invention described herein allows the placement of industry standard coils through a modified microcatheter containing an optical fiber, connected to a laser source, permitting user-determined detachment at any length along the coil while the catheter remains in the patient. This invention also may be applicable to non-flow diverting and flow-diverting stents or other catheter delivered implants such as but not limited to detachable balloons.

In one example embodiment, a microcatheter is modified to comprise an optical fiber running along the length of the microcatheter from the proximal end to the tip at the distal end. At the proximal end, the optical fiber is connected to a laser source. At the tip, a notch or angled cut is made in the optical fiber. This notch/cut is made such that the light passing through the optical fiber is redirected at a near perpendicular angle for the purpose of selectively cutting an object being passed through the microcatheter. For example, a coil in a coil embolizing procedure.

In another example embodiment, a method of manufacturing a microcatheter is disclosed, wherein the microcatheter comprises an embedded optical fiber connected to a laser source. At the distal end, the optical fiber is notched or cut and aligned in the tip of the microcatheter to redirect the light towards the interior of the microcatheter such that a material being passed through the microcatheter may be selectively cut by the user by toggling the laser source.

In another example embodiment, a method of coil embolization is disclosed wherein the coil is delivered via a microcatheter modified with an optical fiber embedded along the length of the microcatheter, wherein the distal end of the optical fiber is notched or cut such that a laser in the optical fiber is redirected towards the interior of the tip of the microcatheter for the purpose of selectively cutting the coil as it is passed through the distal end of the microcatheter.

In another example embodiment, a method of implant detachment during a catheter-based implant procedure is disclosed, wherein the microcatheter has been modified to comprise an embedded optical fiber, the optical fiber comprising a notch/cut at the tip of microcatheter such that a laser passed through the optical fiber from a connected laser source emits from the notch/cut to selectively cut the implant being delivered, thereby acting as the detachment mechanism for the microcatheter.

In one example embodiment, the modified microcatheter may be used in a coil embolization procedure to treat an aneurysm. The modified microcatheter may provide improved functionality to the user by circumventing the need for fixed detachment zones on coils. Instead, a continuous coil may be utilized, and the user may activate the laser source to detach coil segments at user-determined points. This may provide improved coil structural integrity and remove the risk of improperly sized coil segments.

In accordance with some embodiments, a method of detachment when performing a catheter delivered implant procedure comprises a catheter or microcatheter, the catheter modified to embed an optical fiber running along the length of the catheter. The embedded optical fiber modified to have a notch or cut in the distal end of the optical fiber, the notch or cut made such that a laser passing through the optical fiber is redirected at an object or material passing through the distal end of the catheter for the purpose of cutting the object or material, and the proximal end of the optical fiber being connected to a laser source.

In some embodiments, the modified catheter is used to allow a user performing catheter based implants to selectively detach objects or materials being delivered by the pusher wire via a laser, that when activated causes a laser beam to pass through the optical fiber embedded in the catheter and exit the optical fiber through a notch or cut made at the distal end of the optical fiber, thereby cutting off and detaching said object or material being delivered by the pusher wire inside the catheter.

Shown in FIG. 1 is an industry standard microcatheter configured for coil embolization. The microcatheter comprises at least the wall 102, a coil 104, and a pusher wire 106. The wall 102 provides a barrier for the microcatheter and houses the various internal components while maintaining flexibility and steerability. The coil 104 is the implant for the coil embolization procedure. The pusher wire 106 allows the user to push, pull, grab, release, and otherwise generally interact as necessary for various procedures. In this example, it is used to deliver the coil 104.

In a traditional microcatheter used for catheter-based implant procedures, various detachment mechanisms are used to detach deliverable implants including but not limited to mechanical, electrolytic, fusible-link, etc. In coil embolization, for example, these detachment mechanisms typically require that coils include designated detachment sites therefore risking the coil segments being too short or too long for the procedure, or premature detachment.

In the present invention, a detachment mechanism is provided that overcomes this by allowing coils of any length to be used as determined by the user. This is achieved by utilizing a laser-based detachment mechanism, thereby allowing a coil without designated detachment sites to be used. Other catheter-based implant procedures that may benefit from a user-designated detachment site will be appreciated by those of ordinary skill in the art.

Figure 2:
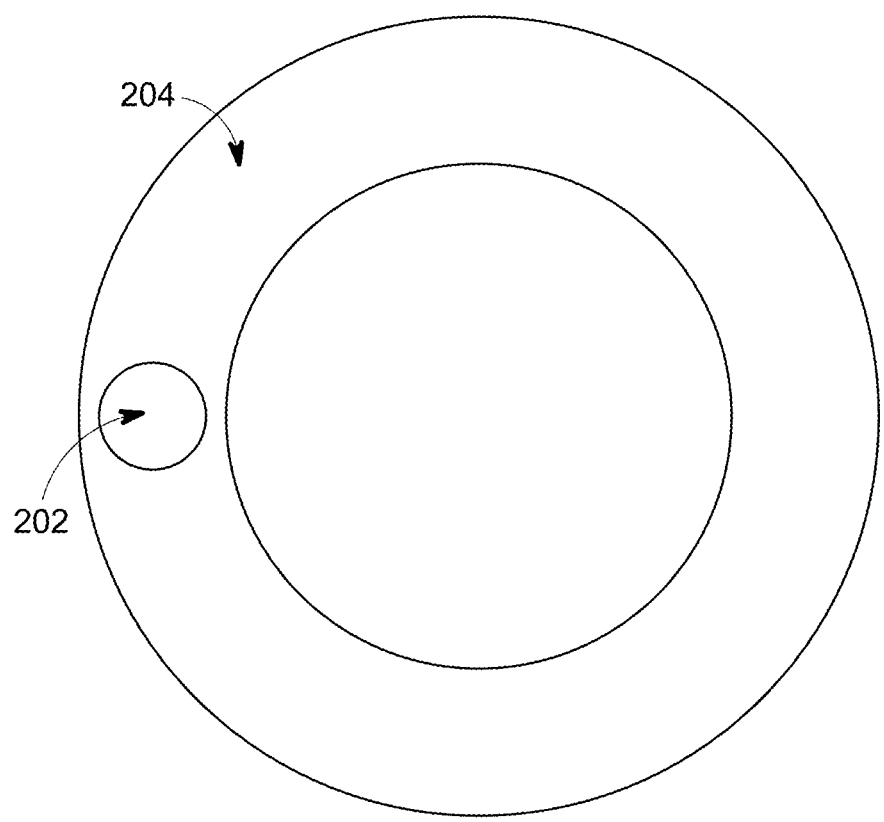
FIG. 2 is an exemplary embodiment of the present invention showing an optical fiber embedded in a catheter.

Shown in FIG. 2 is an example embodiment of the present disclosure. The optical fiber 202 is embedded in the microcatheter 204.

Microcatheters are extremely complex objects of manufacture as they must be small enough to operate intravenously or intraarterially yet maintain several important properties such as kink-resistance, pushability, trackability, and sufficient durometer. Further, different microcatheters will vary in their composition to meet different physical properties to appropriately address various use cases.

For these reasons, it should be appreciated that various methods of manufacture that allow for the optical fiber 202 to be embedded into a microcatheter may be developed as necessary for the respective manufacturer and use cases of the respective microcatheter. Those of ordinary skill in the art will appreciate that alternative constructions may be suitable to fit various conditions, such as specialized procedures, ease of manufacture, cost, etc. In some embodiments, the optical fiber may be embedded in the plastic molding comprising the outer wall of the microcatheter as shown in FIG. 2. In other embodiments, the optical fiber 202 may be embedded interior to the outer wall, fixed to the microcatheter, or housed inside the microcatheter in any fashion appropriate for the application. Thus, the exact way the optical fiber is embedded in the microcatheter is not meant to be a limiting aspect of the present invention.

Figure 3:
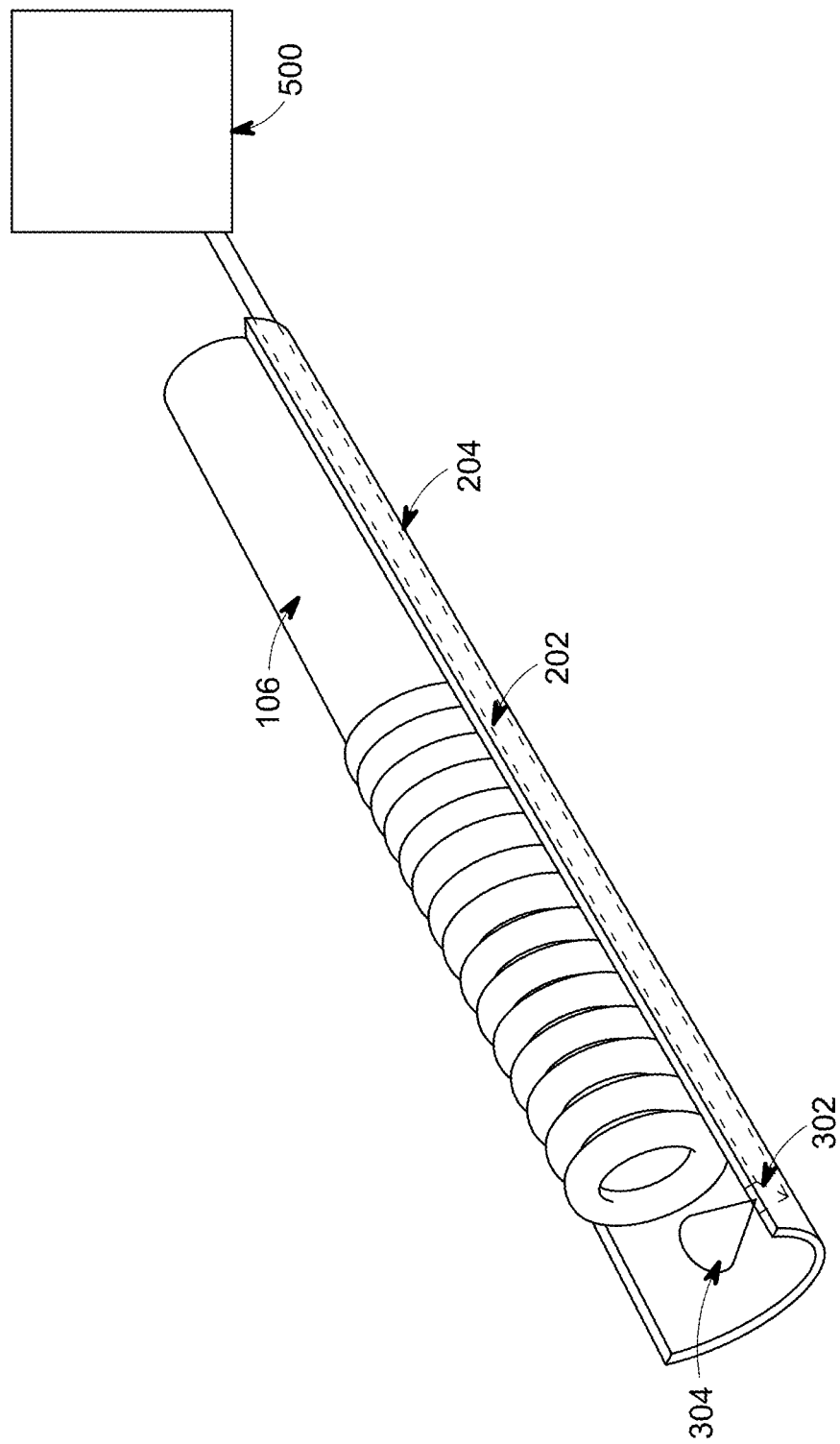
FIG. 3 is an exemplary embodiment of the present invention showing a catheter that has been modified with an embedded optical fiber and with the top outer wall removed such that the internal structure may be seen.

Shown in FIG. 3 is another example embodiment. The standard microcatheter design is modified to include the embedded optical fiber 202 along the length of the microcatheter. At the distal end of the microcatheter, near the tip, the optical fiber 202 is notched or cut at point 302. Light is emitted from the optical fiber 202 as shown at point 304.

When an optical fiber is appropriately notched or cut, total internal reflection is disrupted, and light is emitted perpendicularly to its original path. This phenomenon is leveraged in the present invention to act as the detachment mechanism in the modified catheter. By making a notch or cut in the distal end of the optical fiber, the beam from the laser source is directed out of the notch/cut towards the interior of the catheter tip such that an object or material being delivered through the tip of the catheter may be selectively cut by the user when the laser source is activated. By modifying parameters such as pulse width, power, duration, etc., different materials may be appropriately cut. For example, to cut industry standard coils in a coil embolization procedure used to treat an aneurysm.

In an example embodiment, a user wishes to perform a catheter-based implant procedure. A standard microcatheter is modified to comprise an optical fiber embedded along the length of the microcatheter as shown in FIG. 3. A notching is made in the optical fiber, shown at point 302, made such that when light is passed through the optical fiber 202, the light is redirected inwards, as shown at 304. A pusher wire may be passed through the interior opening of the microcatheter to deliver an implant through the tip of the microcatheter. If the user determines that the implant should be detached, the user may position the implant in front of point 304 at the point which they wish the implant to be cut. Once in position, the user may toggle the laser source connected to the optical fiber, and the notch made at point 302 will emit the laser as shown at point 304 thereby cutting the implant at the desired location.

Figure 4:
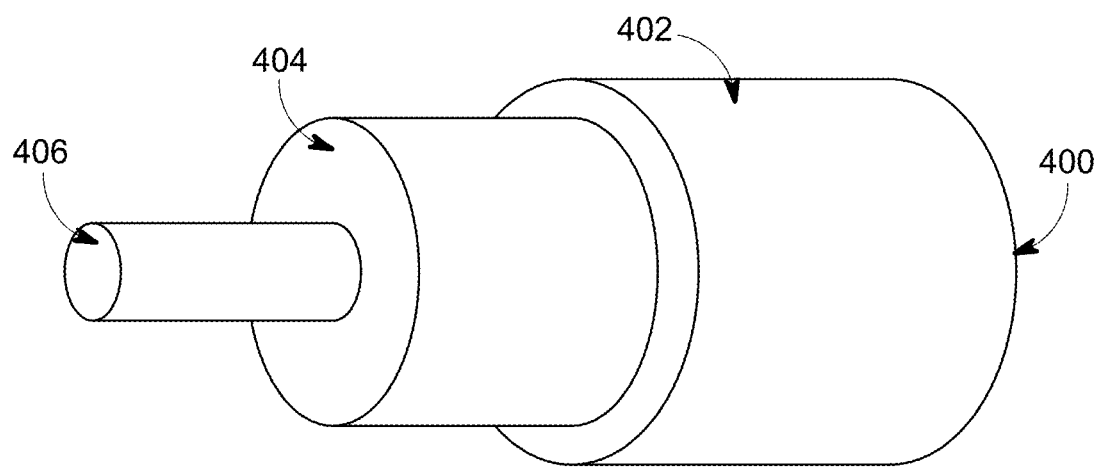
FIG. 4 is an example of an optical fiber standard in the industry.

FIG. 4 shows an example of an optical fiber 400 that may be embedded in the modified catheter disclosed herein. The optical fiber 400 is standard in the industry. The optical fiber 400 comprises a buffer 402, cladding 404, and fiber 406.

The fiber 406 serves as the medium through which the light from the laser source will travel. The cladding 404 serves to reflect light inward, trapping the light inside the fiber 406. The buffer 402 is an outer coating that generally protects the interior. The optical fiber 402 may be any single mode optical fiber that one of ordinary skill in the art would couple with the chosen laser source.

In some embodiments, an industry standard 5 or 10 um silica single mode fiber may be used. The buffer 402 may be approximately 250 um, the cladding 404 may be approximately 125 um and made of acrylate, and the core fiber 406 may be approximately 10 um.

Fiber lasers have become widespread in modern industries for uses from cleaning to cutting. Their relative simplicity to manufacture, small, compact footprint, and capacity to output high pulse energy at lower average power makes them an improvement on industry standard Nd-YAG lasers. Fiber lasers typically require that the active fiber is doped with a rare earth element, such as Ytterbium, Erbium, or Thulium. In an exemplary embodiment of the present invention, the optical fiber embedded in the modified catheter is connected to a Ytterbium nanosecond pulse fiber laser. However, one of ordinary skill in the art will appreciate that alternative lasers may be used. For the purposes of the present invention, any laser source may be used so long as it may act in accordance with embodiments of the detachment mechanism for catheter-based implants described herein.

Figure 5:
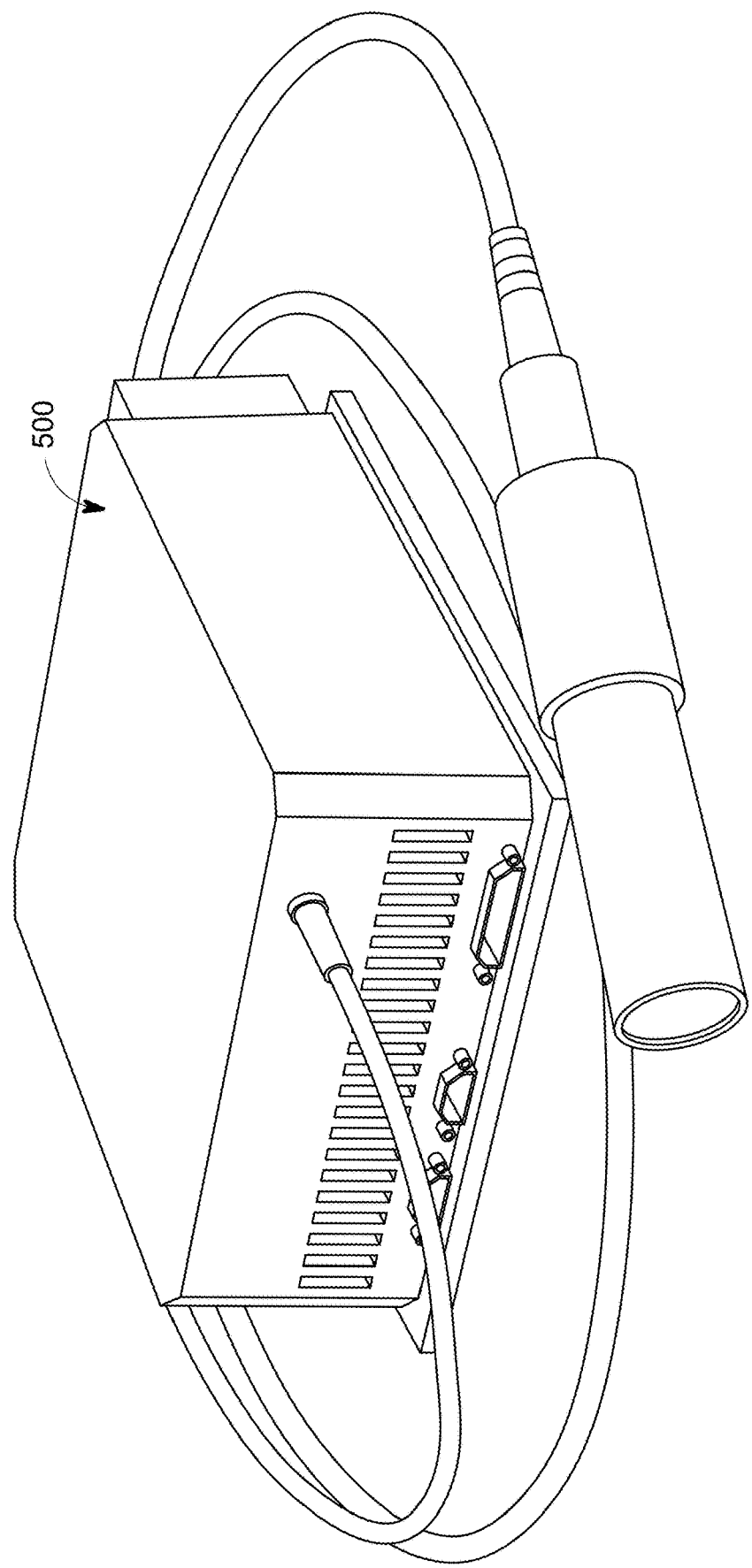
FIG. 5 is an exemplary embodiment of a laser that may be connected to the optical fiber in the modified catheter disclosed herein.

FIG. 5 shows an example embodiment of a ytterbium nanosecond pulse fiber laser that may be used as the laser source for the modified microcatheter disclosed herein. The laser may have variable parameters such as pulse width and power such that selective obliteration of the material or object being passed through the microcatheter is possible without degrading the microcatheter or surrounding tissue.

The laser source connected to the optical fiber delivers the laser beam capable of cutting the object or material being passed through the microcatheter and serves as the detachment mechanism of the modified microcatheter disclosed herein.

The laser source could be a compact fiber or diode-based unit, approximately 1 um wavelength, an industry standard cutting wavelength with high absorption percentage for many metals. Pulse width and power are tunable for selective obliteration of the implant at desired length without degrading the catheter or surrounding tissue.

In some embodiments, the laser source uses a fixed pulse duration of 100 ns, average power from 10 w to 100 w, repetition rate from 2 kHz to 500 kHz, and pulse energy of approximately 1 mJ.

The embodiments described herein may also be scalable to accommodate various applications such as with respect to different size and configurations of catheters and/or microcatheters. Various components of embodiments described herein can be added, removed, reorganized, modified, duplicated, and/or the like as one skilled in the art would find convenient and/or necessary to implement a particular application in conjunction with the teachings of the present disclosure. Moreover, specialized features, characteristics, materials, components, and/or equipment may be applied in conjunction with the teachings of the present disclosure as one skilled in the art would find convenient and/or necessary to implement a particular application in light of the present disclosure.

Many modifications and other embodiments of the present disclosure set forth herein will come to mind to one skilled in the art to which this disclosure pertains having the benefit of the teachings presented in the foregoing descriptions and the associated drawings. Therefore, it is to be understood that the present disclosure is not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated, in light of the present disclosure, that different combinations of elements and/or functions can be provided by alternative embodiments without departing from the scope of the appended claims. In this regard, for example, different combinations of elements and/or functions than those explicitly described above are also contemplated as can be set forth in some of the appended claims. Although specific terms are employed herein, they are used in a generic and descriptive sense only and not for purposes of limitation.

What is claimed:

1. A system comprising:
    a catheter defining a distal tip; and
    a laser source;
        wherein the laser source emits a fixed pulse laser beam adapted to selectively cut catheter delivered implants, including embolization coils and stents, being passed through the distal tip of the catheter;
    wherein the catheter comprises:
        an outer wall;
        a pusher wire interior to the outer wall; and
        an optical fiber embedded in the catheter,
        wherein an exposed portion of the distal end of the optical fiber defines at least one of a notch or angled cut such that a fixed pulse laser beam from the laser source passed through the optical fiber is emitted inwards from the at least one of the notch or the angled cut to cut the catheter delivered implant being passed through the distal tip of the catheter, and
        wherein the laser source is connected to the optical fiber embedded in the catheter.

2. The system of claim 1, wherein the catheter is a microcatheter configured for catheter delivered implants.

3. The system of claim 2, wherein an outer diameter of the distal tip of the microcatheter is between 1.0 Fr and 4.0 Fr.

4. He system of claim 2, wherein a length of the microcatheter is between 50 cm and 200 cm.

5. The system of claim 1, wherein the laser source connected to the optical fiber is a ytterbium nanosecond pulse fiber laser.

6. The system of claim 1, wherein the laser source is configured to output a laser with a fixed pulse of 100 nano seconds with 1 mJ pulse energy.

* * * * *